United States Patent [19]

Kerr et al.

[11] 3,980,585

[45] Sept. 14, 1976

[54] CATALYST AND PROCESS FOR PREPARING MALEIC ANHYDRIDE FROM $C_4$ HYDROCARBONS

[75] Inventors: Ralph O. Kerr; Bruno J. Barone, both of Houston, Tex.

[73] Assignee: Petro-Tex Chemical Corporation, Houston, Tex.

[22] Filed: May 28, 1974

[21] Appl. No.: 473,489

[52] U.S. Cl. .............................. 252/437; 252/435; 260/346.8 M
[51] Int. Cl.² ......................................... B01J 27/18
[58] Field of Search ............................. 252/435, 437

[56] References Cited
UNITED STATES PATENTS

| | | | |
|---|---|---|---|
| 3,086,026 | 4/1963 | Wiebusch | 252/437 X |
| 3,156,705 | 11/1964 | Kerr | 252/435 X |
| 3,156,706 | 11/1964 | Kerr | 252/435 X |
| 3,238,254 | 3/1966 | Kerr | 252/437 X |
| 3,385,796 | 5/1968 | Kerr | 252/435 X |
| 3,433,823 | 3/1969 | McMahon | 252/437 X |
| 3,478,063 | 11/1969 | Friedrichsen et al. | 252/435 X |
| 3,484,384 | 12/1969 | Kerr | 252/437 |
| 3,557,021 | 1/1971 | Coyne et al. | 252/437 X |
| 3,736,354 | 5/1973 | Yanagita et al. | 252/437 X |

*Primary Examiner*—Patrick P. Garvin
*Attorney, Agent, or Firm*—N. Elton Dry; Kenneth J. Johnson

[57] ABSTRACT

A catalyst complex useful for converting normal $C_4$ hydrocarbons to maleic anhydride in vapor phase comprising as components vanadium, phosphorus, copper, an element selected from the group of Te, Zr, Ni, Ce, W, Pd, Ag, Mn, Cr, Zn, Mo, Re, Sm, La, Hf, Ta, Th, Co, U, and Sn, preferably with an alkali or alkaline earth metal.

3 Claims, No Drawings

CATALYST AND PROCESS FOR PREPARING MALEIC ANHYDRIDE FROM C₄ HYDROCARBONS

BACKGROUND OF THE INVENTION

The present invention relates an improved process for the preparation of maleic anhydride from normal C₄ hydrocarbons by the reaction of oxygen with the hydrocarbon in vapor phase over a particular novel catalyst.

The production of dicarboxylic acid anhydride by catalytic oxidation of hydrocarbons is well known. The current principal route for the production of maleic anhydride is the catalytic oxidation of benzene. The direct production of maleic anhydride from the C₄ hydrocarbons has been desirable in the past, but is now even more desirable in view of the particular world shortage of benzene. It can be readily appreciated that direct oxidation of C₄ hydrocarbons would be a hydrocarbon conservation, since for each mol of maleic anhydride prepared from benzene, one mole of benzene, molecular weight 78 is consumed whereas for each mol of the C₄ only 54 to 58 mol weight of hydrocarbon is consumed. The benzene process has consistently produced high conversions and selectivities. Although processes for the oxidation of aliphatic hydrocarbons are reported in the literature, there are certain defects and inadequacies in these processes such as short catalyst life and low yields of product. Furthermore, although many of the prior art methods are generically directed to "aliphatic" hydrocarbons, they are in all practical aspects directed to unsaturated aliphatic hydrocarbons.

A more desirable process for producing maleic anhydride would be a direct oxidation of n-butane. There are several advantages. Principal among these is the greater availability of n-butane as compared to n-butenes or butadiene. Also n-butenes may have higher economic petrochemical utilization than the n-butanes, which are now, often wastefully burned as cheap fuel.

In an early series of patents one of the present inventors developed a unique group of vanadium-phosphorus, oxidation catalysts, i.e., U.S. Pat. Nos. 3,156,705; 3,156,706; 3,255,211; 3,255,212; 2,255,213; 2,288,721; 3,351,565; 3,366,648; 3,385,796 and 3,484,384. These processes and catalysts proved highly efficient in the oxidation of n-butenes to maleic anhydride.

SUMMARY OF THE INVENTION

It has now been discovered that vanadium-phosphorus-oxygen complex type catalyst modified with copper and a Me component, are excellent oxidation catalysts for the conversion of n-C₄ hydrocarbons to maleic anhydride. Surprisingly, the present catalysts are excellent for the direct oxidation of n-butane to maleic anhydride. In addition to n-butane, n-butene, and butadiene can also be used as feeds. The catalyst contains only a minor amount of copper and the Me component. The Me component is generally a metal or metalloid element.

The precise structure of the present complex catalyst has not been determined, however, the complex may be represented by formula

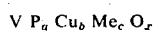

wherein Me is Te, Zr, Ni, Ce, W, Pd, Ag, Mn, Cr, Zn, Mo, Re, Sm, La, Hf, Ta, Th, Co, U, Sn, or mixtures thereof, $a$ is 0.90 to 1.3, $b$ is 0.005 to 0.3 and $c$ is 0.001 preferably 0.005 to 0.25. This representation is not an empirical formula and has no significance other than representing the atom rato of the active metal components of the catalyst. The $x$ in fact has no determinate value and can vary widely depending on the combinations within the complex. That there is oxygen present is known and the $O_x$ is representative of this. A more specific group of Me components is Te, Zr, Ni, Ce, W, Pd, Ag, Mn, Cr, Mo, Re, Hf, Ta, Th, Co, U, Sn or mixtures thereof.

A more preferable catalyst is one wherein Me is Te, Ni, Ce, Cr, Mo, Re, Hf, Ta, U, or mixtures thereof.

In one embodiment of the present invention the catalyst complex comprises vanadium-phosphorus, copper, a second metal, Me, and an alkali or alkaline earth metal, (Alk-metal) of group IA of IIA of the Periodic Table of Elements.* This complex may be represented by the configuration

wherein Me, $a$, $b$, $c$, and $x$ are as described above and Alk is a metal selected from the group of elements of Groups IA and IIA of the Periodic Table of Elements, and $d$ is 0.001 to 0.1. Particular Group IA and IIA elements for the present invention are Li, Na, K, Rb, Cs, Be, Mg, Ca, Sr and Ba. Even more preferably Li, Na, Mg and Ba.

*Handbook of Chemistry and Physics, 51st Edition, 1970–71, The Chemical Rubber Company, Cleveland, Ohio, 1970, p. B–3.

DETAILED DESCRIPTION OF THE INVENTION

The catalyst may be prepared in a number of ways. The catalyst may be prepared by dissolving the vanadium, phosphorus, copper, Me and Group IA and IIA components (referred to herein as alk metals) in a common solvent, such as hot hydrochloric acid and thereafter depositing the solution onto a carrier. The catalyst may also be prepared by precipitating the metal compounds, either with or without a carrier, from a colloidal dispersion of the ingredients in an inert liquid. In some instances the catalyst may be deposited as molten metal compounds onto a carrier; however, care must be taken not to vaporize off any of the ingredients such as phosphorus. The catalyst may also be prepared by heating and mixing anhydrous forms of phosphorus acids with vanadium compounds, copper compounds. Me compounds, and the alk - metal compound. The catalysts may be used as either fluid bed or fixed bed catalysts. In any of the methods of preparation heat may be applied to accelerate the formation of the complex. Although some methods of catalyst preparation are preferred, any method may be used which results in the formation of the catalyst complex containing the specified ratios of vanadium, copper, Me elements, phosphorus and alk metal.

One method to obtain catalysts which produce high yields of maleic anhydride upon oxidation of C₄ hydrocarbons is whereby the catalyst complex is formed in solution and deposited as a solution onto the carrier. According to one solution method, the vanadium is present in solution with an average valence of less than plus 5 in the finally formed complex in solution. Preferably the vanadium has an average valency of less than plus 5 at the time the solution of catalyst complex is deposited onto the carrier, if a carrier is used. The reduced vanadium with a valence of less than 5 may be obtained either by initially using a vanadium compound wherein the vanadium has a valence of less than 5 such as vanadyl chloride, or by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound may be dissolved in a reducing solvent, such as hydrochloric acid, which solvent functions not only to form a solvent for the reaction, but also to reduce the valence of the vanadium compound to a valence of less than 5. For example, a vanadium compound, a copper compound, a tellurium compound, phosphorus compound and alk metal compound may be dissolved in any order in a suitable reducing solvent and the formation of the complex allowed to take place. Preferably, the vanadium compound is first dissolved in the solvent and thereafter the phosphorus, copper, tellurium and alk metal compounds are added. The reaction to form the complex may be accelerated by the application of heat. The deep blue color of the solution shows the vanadium has an average valence of less than 5. The complex formed is then, without a precipitation step, deposited as a solution onto a carrier and dried. In this procedure, the vanadium has an average valence of less than plus 5, such as about plus 4, at the time it is deposited onto the carrier. Generally, the average valence of the vanadium will be between about plus 2.5 and 4.6 at the time of deposition onto the carrier.

When the above described solution method is employed, reducing agents for the vanadium may be either organic or inorganic. Acids such as hydrochloric, hydroiodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed, but which have not been given as desirable catalysts are organic aldehydes such as formaldehyde and acetaldehyde; alcohols such as pentaerythritol, diacetone alcohol and diethanol amine. Additional reducing agents are such as hydroxyl amines, hydrazine, and nitric oxide. Nitric acid and similar oxidizing acids which would oxidize the vanadium from a valence of 4 to 5 during the preparation of the catalyst should be avoided. Generally the reducing agents form oxysalts of vanadium. For example, if $V_2O_5$ is dissolved in hydrochloric or oxalic acid, the corresponding vanadium oxysalts are produed. These vanadium oxysalts should have as the salt forming anion an anion which is more volatile than the phosphate anion.

According to this method, the time at which the copper, Me and metal compounds are incorporated into the solution is not critical so long as it is in solution before the catalyst complex is coated onto the carrier. The copper, Me and alk metal compounds may be added after the vanadium compound and the phosphorus compound have been reacted or may be added either before, at the same time or after either the vanadium or phosphorus compound has been added.

Any vanadium, copper, Me, phosphorus and alk metal compounds may be used as starting materials which when the compounds are combined and heated to dryness in air at a temperature of, for example, 300°–350° C. will leave as a deposit a catalyst complex having relative proportions within the described ranges. In the solution methods, preferred are vanadium, copper, Me, phosphorus and alk metal compounds which are essentially completely soluble in boiling aqueous hydrochloric acid at 760 mm. of mercury, containing 37 percent by weight hydrochloric acid. Generally, phosphorus compounds are used which have as the cation an ion which is more volatile than the phosphate anion, for example, $H_3PO_4$. Also, generally any vanadium, copper of Me compound which has as an anion an anion which is either the phosphate ion or an ion which is more volatile than the phosphate anion, for example, vanadyl chloride, copper (II) chloride or tellurium tetrachloride may be used.

In this method, the catalyst complex containing vanadium, copper, Me, phosphorus and Group I or IIA elements may be formed by simply causing the combination of each of the ingredient components in a solution or dispersion. Heat may be applied to accelerate the formation of the complex and one method of forming the complex is by causing the ingredients to react under reflux conditions at atmospheric pressure. Under reflux conditions this solution reaction generally takes about one to two hours.

Although the catalysts prepared by this method may be separately formed and used as pellets it ay be more economical and practical to deposit this material on a carrier such as aluminium oxide, silica or niobium oxide. Before the carrier is combined with the catalyst the solution of catalyst is preferably concentrated to a solution which contains from about 30 to 80 percent volatiles and better results have been obtained when there is from about 50 to 70 percent volatiles by weight. The carrier may be added to the catalyst solution or the catalyst solution may be poured onto the carrier. Less desirably, the Alundum or other carrier may be present during the whole course of reactions to provide the desired vanadium-oxygen phosphorus-alkali metal complex. After the catalyst complex has been coated onto the carrier, the vanadium may be converted to a more active form by heating in the presence of an oxidizing gas.

Another example of the catalyst preparation is to mix with heating at a temperature of about 100°C. to 600°C. an anhydrous phosphoric acid such as orthophosphoric acid, pyrophosphoric acid, triphosphoric acid or metaphosphoric acid with a vanadium compound such as vanadium pentoxide or ammonium metavanadate, a copper compound such as copper (II) chloride, a Me compound such as tellurium tetrachloride and an alkali such as potassium chloride. After the exothermic reaction between the ingredients the catalyst may be used. The reaction mixture may be formed onto carriers or shaped into forms such as pellets prior to the reaction to form the catalyst.

Another example of the preparation of the catalyst complex is to dissolve the copper, Me and alk metal compounds and a vanadium compound such as ammonium metavanadate or vanadium pentoxide in an aqueous solution of phosphoric acid. After the components have been dissolved the solution is heated until precipitation occurs. The precipitant can then be dried and used as a catalyst, or a carrier may be combined with the liquid phase either before or after the precipitation.

In the various methods of preparation any vanadium, copper, Me, phosphorus and alk metal compounds may be used as starting materials which when the compounds are combined and heated to dryness in air at a temperature of, for example, 300°–350° C. will leave as a deposit a catalyst complex having relative proportions within the above described ranges.

A new method of catalyst preparation which is simple, easy to handle and avoids some of the problems of these prior methods has been devised by Dr. Ralph O. Kerr, one of the coinventors herein. In this method a solution of the vanadium component is prepared by adding a portion of the reducing agent, such as oxalic acid and isopropanol solution to be employed, to a solution of water and phosphoric acid and heating this mixture to a temperature generally of around 50° – 80° C. A vanadium compound such as $V_2O_5$ is added incrementally to this heated mixture with stirring. The blue solution which indicates vanadium of average valency less than 5, is maintained by added increments of the remaining oxalic acid - isopropanol solution. After concentration of this solution, solutions of copper, alkali and alkaline earth metals and the Me components are added to vanadium solution and this resultant solution concentrated to a paste-like consistency, which may be coated on a carrier or mixed with a carrier, heated at moderate temperatures, i.e., 250° – 500° C. for a few minutes to several hours and prepared in pellets or chips.

The alk-metal may suitably be introduced as compounds such as alkali and alkaline earth metal salts with examples being lithium acetate, lithium bromide, lithium carbonate, lithium chloride, lithium hydroxide, lithium iodide, lithium oxide, lithium sulfate, lithium orthophosphate, lithium meta-vanadate, potassium sulfate, potassium chloride, potassium hydroxide, sodium chloride, sodium hydroxide, rubidium nitrate, cesium chloride, beryllium nitrate, beryllium sulfate, magnesium sulfate, magnesium bromide, magnesium carbonate, calcium carbonate, calcium chromite, strontium chloride, strontium chromate, barium acetate, barium chlorate, barium tellurate, radium carbonate and the like. Mixtures of two or more alk metal compounds may be used, such as a mixture of lithium hydroxide and sodium chloride or a mixture of lithium chloride and potassium chloride. Preferred alk-metal elements are lithium, sodium and potassium, and mixtures thereof, with lithium being particularly preferred. When the above described solution method of catalyst preparation is employed, the alkali metal compound will suitably be an alkali metal compound which either has a phosphate anion as the anion, that is a compound such as lithium phosphate, or a compound which has an anion which is more volatile than the phosphate anion.

As the source of phosphorus, various phosphorus compounds may be used, such as metaphosphoric acid, triphosphoric acid, pyrophosphoric acid, ortho-phosphoric acid, phosphorus pentoxide, phosphorus oxyiodide, ethyl phosphate, methyl phosphate, amine phosphate, phosphorus pentachloride, phosphorus trichloride, phosphorus oxybromide and the like.

Suitable copper compounds are the various compounds such as the copper halides, phosphates, oxides, carbonates, sulfates, nitrates, acetates, hydrides, and so forth. Metallic copper may be used. Generally copper compounds are used which either have the phosphate anion as the anion or which have an anion which is more volatile than the phosphate anion. Copper compounds which are soluble in hydrochloric acid are preferred. Compounds such as cuprous oxide, cupric oxide, cuprous chloride, cuprous sulfate, cuprous or cupric sulfide, cupric lactate, cupric nitrate, cupric phosphate, cuprous bromide, cuprous carbonate, cupric sulfate, cupric oxychloride, cuprous hydroxide, cuprous sulfite, cupric acetate, and the like, are useful as starting materials.

The Me component (including Te) is also suitably introduced by employing the various compounds thereof such as the acetates, carbonates, chlorides, bromides, oxides, hydroxides, nitrates, chromates, chromites, tellurates, sulfides, phosphates and the like. These compounds are entirely conventional and those of ordinary skill in the art know these materials and can readily determine suitable compounds to prepare the catalyst, with little, if any, experimentation. A few illustrative compounds are tellurium tetrachloride, nickel chloride, cerium (III) nitrate, tungsten dioxide, silver nitrate, manganese (II) sulfate, chromium sulfate, zinc oxalate, rhenium oxide, samarium oxalate, lanthanum hydroxide, thorium nitride, cobalt (II) orthostannate, uranyl sulfate, iron (III) oxide, tin (IV sulfate, boron trichloride, and similar compounds.

Suitable vanadium compounds useful as starting materials are compounds such as vanadium pentoxide, ammonium metavanadate, vanadium trioxide, vanadyl chloride, vanadyl dichloride, vanadyl trichloride, vanadium sulfate, vanadium phosphate, vanadium tribromide, vanadyl formate, vanadyl oxalate, metavanadic acid, pyrovanadic acid, and the like. Mixtures of the various vanadium, Me, phosphorus and copper compounds may be used as starting materials to form the described catalyst complex.

One preferred species of the present vanadium - phosphorus - oxygen complex catalyst contains a minor amount of copper, tellurium and an element or compound of Group IA of the Periodic Table of elements. The catalyst contains vanadium, phosphorus, copper, tellurium and the Group IA component and oxygen chemically bonded together as a complex. Lithium is the preferred Group IA element for use in this species.

Copper is present in minor amounts but in a relatively wide range of about 0.04 to 0.20 atom of copper per atom of vanadium. The copper may be considered an "active" along with vanadium, in that it is undergoing oxidation and reduction. Phosphorus, on the other hand, is a vanadium modifier and tellurium may serve the same purpose in regard to copper. These components of the complex catalyst may serve other functions or may be characterized by others in a different manner, however, the characterization provided above may aid in understanding the mechanism of this catalyst.

The tellurium is present in an amount of 0.001 to 0.2 atom per atom of vanadium and is apparently essential to moderate the activity of catalyst complex, i.e., probably the copper component.

The function of the Group IA element is not completely understood but superior results are obtained when the catalyst contains these elements. Longer useful catalyst life has been observed when the IA element is present, probably due, at least in part, to the partially stabilizing effect of the alkali on phosphorus, copper and tellurium.

The atomic ratio of the total atoms of Group IA elements to vanadium should be about 0.003 to 0.08 atom of alkali per atom of vanadium. The preferred amount of alkali is about 0.01 to 0.04 atom per atom of vanadium.

For the P-V-Cu-Te-IA species and ratios of Cu to V thereof defined above the amount of phosphorus present is critical and has been determined to be 1.05 to 1.2 atoms of phosphorus per atom of vanadium. The preferred amount of phosphorus is in the very narrow range of 1.10 to 1.15 atoms per atom of vanadium. Amounts of phosphorus outside of the broadest range specified have given low yields of maleic anhydride. Within the preferred range of phosphorus content, catalyst gives superior results.

A catalyst support, if used, provides not only the required surface for the catalyst, but gives physical strength and stability to the catalyst material. The carrier or support normally has a low surface area, as usually measured, from about 0.001 to about 5 square meters per gram. A desirable form of carrier is one which has a dense non-absorbing center and a rough enough surface to aid in retaining the catalyst adhered thereto during handling and under reaction conditions. The carrier may vary in size but generally is from about 2½ mesh to about 10 mesh in the Tyler Standard screen size. Alundum particles as large as ¼ inch are satisfactory. Carriers much smaller than 10 to 12 mesh normally cause an undesirable pressure drop in the reactor, unless the catalysts are being used in a fluid bed apparatus. Very useful carriers are Alundum and silicon carbide or Carborundum. Any of the Alundums or other inert alumina carriers of low surface may be used. Likewise, a variety of silicon carbides may be employed. Silica gel may be used.

Other materials which can serve as carriers are $Nb_2O_5$, $WO_3$, $Sb_2O_3$ and mixtures of these and other supports. The support material is not necessarily inert, that is, the particular support may cause an increase in the catalyst efficiency by its chemical or physical nature of both.

The amount of the catalyst complex on the carrier is usually in the range of about 15 to about 95 weight percent of the total weight of complex plus carrier and preferably in the range of 50 to 90 weight percent and more preferably at least about 60 weight percent on the carrier. The amount of the catalyst complex deposited on the carrier should be enough to substantially coat the surface of the carrier and this normally is obtained with the ranges set forth above. With more absorbent carriers, larger amounts of material will be required to obtain essentially complete coverage of the carrier. In a fixed bed process the final particle size of the catalyst particles which are coated on a carrier will also preferably be about 2½ to about 10 mesh size. The carriers may be of a variety of shapes, the preferred shape of the carriers is in the shape of cylinders or spheres. Although more economical use of the catalyst on a carrier in fixed beds is obtained, as has been mentioned, the catalyst may be employed in fluid bed systems. Of course, the particle size of the catalyst used in fluidized beds is quite small, usually varying from about 10 to about 150 microns, and in such systems the catalyst normally will not be provided with a carrier but will be formed into the desired particle size after drying from solution.

Inert diluents such as silica may be present in the catalyst, but the combined weight of the essential active ingredients of vanadium, oxygen, phosphorus, copper, Me, and alk metal should preferably consist essentially of at least about 50 weight percent of the composition which is coated on the carrier, if any, and preferably these components are at least about 75 weight percent of the composition coated on the carrier, and more preferably at least about 95 weight percent.

The oxidation of the n-$C_4$ hydrocarbon to maleic anhydride may be accomplished by contacting, e.g., n-butane, in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the oxidation reactors normally will contain air and about 0.5 to about 2.5 mol percent hydrocarbons such as n-butane. About 1.0 to about 1.5 mol percent of the n-$C_4$ mol percent of the n-$C_4$ hydrocarbon are satisfactory for optimum yield of product for the process of this invention. Although higher concentrations may be employed, explosive hazards may be encountered. Lower concentrations of $C_4$, less than about one percent, of course, will reduce the total yields obtained at equivalent flow rates and thus are not normally economically employed. The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25°C. A preferred feed for the catalyst of the present invention for conversion to maleic anhydride is a n-$C_4$ hydrocarbon comprising a predominant amount of n-butane and more preferably at least 90 mol percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-potassium nitrate eutectic constant temperature mixture. An additional method of temperature control is to use a metal block reactor whereby the metal surrounding the tube acts as a temperature regulating body. As will be recognized by the man skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100°C. above the salt bath temperature. The temperature in the reactor, of course, will also depend to some extent upon the size of the reactor and the $C_4$ concentration. Under usual operating conditions, in compliance with the preferred procedure of this invention, the temperature in the center of the reactor, measured by thermocouple, is about 375+ to about 550°C. The range of temperature preferably employed in the reactor, measured as above, should be from about 400° to about 515°C. and the best results are ordinarily obtained at temperatures from about 420° to about 470°C. Described another way, in terms of salt bath reactors with carbon steel reactor tubes about 1.0 inch in diameter, the salt bath temperature will usually be controlled between about 350° to about 550°C. Under normal conditions, the temperature in the reactor ordinarily should not be allowed to go above about 470°C. for extended lengths of time because of decreased yields and possible deactivation of the novel catalyst of this invention.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered by a number of ways well known to those skilled in the art. For example, the recovery may be by direct condensation or by adsorption in suitable media, with subsequent separation and purification of the maleic anhydride.

In the following examples, two types of reactors were employed. The results of the tests in the two reactors are qualitatively comparable, i.e, an increase in maleic anhydride yield in the smaller equipment will be reflected in the larger equipment, although the absolute numbers are different.

"A" Reactor

The "A" reactor comprised a 4-tube cylindrical brass block (8 inches O.D. × 18 inches) reactor made of alloy 360. The block was heated by two 2500 watt (220 volt) cartridge heaters controlled by means of a 25 amp. theremoelectric proportional controller with automatic reset. Prior to its insulation, the block was tightly wound with a coil of ⅜ inch copper tubing. This external coil was connected to a manifold containing water and air inlets for cooling of the reactor block. The reactors were made of a 304 stainless steel tube, 1.315 inches O.D. and 1.049 inches I.D., 23½ inches long, containing a centered ⅛ inch O.D. stainless steel thermocouple well. The lower end of the reactor was packed with a 1 inch bed of 3 mm pyrex beads. The next 12 inches of the reactor were packed with catalyst (⅛ × ⅛ inch pellets or 6-12 mesh granules) followed by about a 10 inch bed of 3 mm pyrex beads. The gas streams are separately metered into a common line entering the top of the reactor. The reaction vapors are passed through two 2000 ml. gas scrubbing bottles containing 800 ml. of water. The vapors from the scrubbers then go through a wet test meter and are vented. The inlet gases are sampled before entering the reactor and after the water scrubbers. The feed is normally 0.5 to 1.8 mol % $C_4$, e.g., n-butane, in air, adjusted to maintain a desired temperature. In addition, operating temperature can be further controlled by dilution of the air with an inert gas.

The inlet gases and water scrubbed outlet gases were analyzed by gas chromatography using the peak area method. Butane, carbon dioxide and any olefins or diolefins present in the gas streams were determined using a ¼ inch column with a 5 feet foresection, containing 13 wt. % vacuum pump oil on 35/80 mesh chromosorb, followed by a 40 feet section containing 26 wt. % of a 70-30 volume ratio of propylene carbonate to 2,4-dimethylsulfolane on 35/80 mesh chromosorb. The analysis was conducted at room temperature with hydrogen as the carrier gas (100 ml/minute). Carbon monoxide was analyzed on a ¼ inch column with a 3 feet foresection of activated carbon followed by a 6 feet section of 40/50 mesh 5A molecular sieves. This analysis was run at 35° C with helium as the carrier gas (20 psi).

The water scrub solutions were combined and diluted to 3000 ml. in a volumetric flask. An aliquot of this solution was titrated with 0.1 N sodium hydroxide solution to determine maleic acid (first end point) and weak acids in solution and titrated to determine the carbonyls, using hydroxylamine hydrochloride.

"B" Reactor

The "B" reactor employed 300 milliliters of catalyst packed in a 3 foot carbon steel tube, ¾ inch inside diameter, with inert ¼ inch Alundum pellets on top of the catalyst material to a height ⅓ of the height of the catalyst. Some runs in the B procedure were carried out in larger reactors however, the results as reported herein are equivalent with the 3 feet reactor.

The reactors were encased in a 7% sodium nitrate −40% sodium nitrite −53% potassium nitrite eutectic mixture constant temperature salt bath. The reactor was slowly warmed to 400°C. (250°-270° C air passing over catalyst) while passing a gas stream containing 0.5 to 0.7 mol percent n-butane and air over the catalyst beginning at about 280°C. The reactor outlet was maintained at 1 p.s.i.g. After the reactor had reached 400°C., the catalyst was aged by passing the n-butane - air mixture therethrough for 24 hours. The n-butane - air and temperature was increased to obtain a maximum throughput. The n-butane in the feed is increased to 1.0 – 1.5 mol percent to obtain 80 - 90% conversion. The salt bath is operated at a maximum of 420°C. The maximum throughput is achieved in relation to the maximum salt bath temperature and a maximum hot spot of about 450°C. The hot spot is determined by a probe through the center of the catalyst bed. The temperature of the salt bath can be adjusted to achieve the desired relationship between the conversion and flow rates of the n-$C_4$ - air mixture. The flow rate is adjusted to about 85% conversion and the temperature relations given above. Generally, flow rates of about 30 to 75 grams of hydrocarbon feed per liter hour are used. The exit gases were cooled to about 55°-60°C. at about ½ p.s.i.g. Under these conditions, about 30 –50% of the maleic anhydride condenses out of the gas stream. A water scrubber recovery and subsequent dehydration and fractionation were used to recover and purify the remaining maleic anhydride in the gas stream after condensation. The combined maleic anhydride recovered is purified and recovered at a temperature of about 140°-145°C. overhead and 145°C. bottoms temperatures in a fractionator. The purified product had a purity of 99.9+ percent maleic anhydride.

EXAMPLE 1.

The following procedure was employed in preparing the various catalysts modified to achieve the variation in atomic ratios recited in the Examples.

Typical Method of Preparation (90 pts $VP_{1.185} Cu_{0.072} Te_{0.018} Li_{0.017} O_x$ - 10 pts $Nb_2O_5$)

(A)
- $V_2O_5$ = 118.17 g 1.300 mole V
- oxalic acid = 120 g
- Isopropanol = 120 ml
- Water = 2200 ml.
- $H_3PO_4$(85%) = 177.67 g 1.541 mole P.

(B)
- $CuCl_2$ = 12.5 g 0.0936 mole Cu
- LiCl = 0.94 g 0.0221 mole Li
- Water = 50 ml. Other Alk-metal compounds can be used in addition to or in place of LiCl.

(C)
- $TeO_2$ = 3.73 g 0.0234 mole Te
- HCl = 10 ml. In addition to $TeO_2$ or in place thereof the other metal components (Me) of the catalyst are dissolved herein.

(D)
- $Nb_2O_5$ = 26.5 g.

Solutions B and C was prepared by gently warming on a hot plate. Solution A was prepared as follows:

Approximately ½ of the oxalic acid and isopropanol are added to the water along with the phosphoric acid. The 4-liter beaker is stirred on a magnetically stirred hot plate. When the solution reaches 75° C it is maintained at this temperature and the $V_2O_5$ is added in small increments maintaining a blue vanadyl phosphate solution. The remaining oxalic acid and isopropanol are added as needed to maintain the blue solution. This solution is then concentrated to a volume of 700 ml. and is then transferred to a large evaporating dish and the B and C solutions added. Stirring is continued and the solution is concentrated to a pastelike consistancy. The $Nb_2O_5$ is added and slurried with paste. It is then dried in an oven at 130°C. overnight. It is broken up and calcined at 350°C. in an air atmosphere for 6 hours. It is then either used as a chip (6–8 mesh) or ground and compressed into ⅛ × ⅛ inch tablets.

The term yield used herein means conversion $x$ selectivity.

EXAMPLES A1 – A3

These examples were carried out in the A reactor. The effect of several catalyst supports were evaluated. The catalyst composition is represented by the atom ratio $VP_{1.2} Cu_{0.026} Te_{0.026} Li_{0.039} O_x$. Temperature conditions, wt. percent catalyst, conversions and results are given in Table I.

Table I

| Ex. | Support | Wt. % Cat. | Reactor Temp. °C | Hot Spot Temp. °C | Butane Conv. % | % S M. A. | Mol % yld. M. A. |
|---|---|---|---|---|---|---|---|
| A1 | $Nb_2O_5$ | 70 | 450 | 483 | 83.61 | 42.12 | 35.22 |
| A2 | PAC[2] | 70 | 450 | 467 | 59.32 | 56.05 | 33.25 |
| A3 | Celite[3] | 70 | 450 | 470 | 51.93 | 49.13 | 25.51 |

[1]Based on total wt. of catalyst and support.
[2]PAC = Phosphoric acid carrier.
[3]Celite = Johns Manville No. 545 Celite calcined at 1000°C.

EXAMPLES A4 to A13.

These examples demonstrate various Me components found suitable in the V $P_a Cu_b Me_c Alk_d O_x$ type catalysts of the present invention. In a large number of these examples, Te and a second Me component are employed. The method of preparation is that described in Example 1. The active components are specified for each example in atom ratio (except for oxygen) in Table II. The support and total weight % of catalyst and temperatures and results are provided in Table II also. The A apparatus and procedure were used. All catalysts were on stream for at least 100 hours when data was taken on results.

EXAMPLES B1 to B10.

Using the apparatus and procedure B the variation in P ratio was examined. The data presented below in Table III tends to demonstrate the preferred range of atom ratio of phosphorus to vanadium for the species of complex comprising phosphorus, vanadium, copper, tellurium and an alkali or alkaline earth metal (with or without additional Me components). The feed was n-butane ($\cong$ 99% n-butane).

Examples B1 – B3 demonstrate P/V atomic ratios within (B1 and B2) and above (B3) the preferred range. Other comparisons tending to show the detrimental effect of too little phosphorus relative to vanadium are present in examples B4, B5, B8 and B10. The significance of the preferred range of P/V atomic ratio, i.e., 1.05 to 1.2 for the P, V, Cu, Te, Alk-metal O composition is seen to hold even when other components are added, as disclosed, or the amount of carrier is varied.

EXAMPLES B11 to B15.

Employing the procedure and apparatus B a series of runs with related catalyst complex demonstrates the advantage of high weight percent of catalyst complex to carrier. The temperature of the reaction is considerably reduced when the carrier is reduced, while the product distribution to maleic anhydride remains high. This data is shown in Table IV. The feed was $\cong$ 99% n-butane.

EXAMPLES B16 to B34.

These examples demonstrate various of the species of the present inventions and clearly indicate the scope. The catalyst are prepared according to Example 1 and the procedure and equipment of reactor B were employed. The results are given in Table V. The feed was $\cong$ 99% n-butane. All catalysts were on stream for at least 300 hours when data was taken.

Table II

| Example | Catalyst Complex | Support | Wt. % Catalyst | Reactor Temp. °C. | Hot spot Temp. °C. |
|---|---|---|---|---|---|
| A4 | $VP_{1.2}Cu_{0.026}Te_{0.026}Li_{0.039}O_x$ | $Nb_2O_5$ | 70 | 450 | 483 |
| A5 | $VP_{1.2}Cu_{0.026}Te_{0.026}Ni_{0.026}Li_{0.039}O_x$ | $Nb_2O_5$ | 70 | 450 | 474 |
| A6 | $VP_{1.2}Cu_{0.026}Te_{0.026}Ce_{0.026}Li_{0.039}O_x$ | $Nb_2O_5$ | 70 | 450 | 466 |
| A7 | $VP_{1.2}Cu_{0.026}Ce_{0.026}Li_{0.039}O_x$ | $Nb_2O_5$ | 70 | 420 | 445 |
| A8 | $VP_{1.2}Cu_{0.026}Te_{0.026}Ni_{0.03}Li_{0.039}O_x$ | None | 100 | 450 | 482 |
| A9 | $VP_{1.2}Cu_{0.026}Te_{0.026}W_{0.056}Li_{0.039}O_x$ | $Nb_2O_5$ | 70 | 440 | 491 |
| A10 | $VP_{1.2}Cu_{0.026}Cr_{0.026}Te_{0.052}Li_{0.039}O_x$ | None | 100 | 420 | 450 |
| A11 | $VP_{1.185}Cu_{0.072}Te_{0.018}Na_{0.017}O_x$ | $Nb_2O_5$ | 10 | 440 | 463 |
| A12 | $VP_{1.185}Cu_{0.072}Te_{0.018}Ba_{0.017}$ | $Nb_2O_5$ | 10 | 440 | 465 |
| A13 | $VP_{1.185}Cu_{0.072}Te_{0.018}Mg_{0.937}$ | $Nb_2O_5$ | 10 | 440 | 457 |

| Example | Catalyst Complex | Butane[1] Conv. % | % Selectivity M. A. | Mol % Yld. M. A. |
|---|---|---|---|---|
| A4 | $VP_{1.2}Cu_{0.026}Te_{0.026}Li_{0.039}O_x$ | 83.61 | 42.12 | 35.22 |
| A5 | $VP_{1.2}Cu_{0.026}Te_{0.026}Ni_{0.026}Li_{0.039}O_x$ | 62.21 | 52.76 | 32.82 |
| A6 | $VP_{1.2}Cu_{0.026}Te_{0.026}Ce_{0.026}Li_{0.039}O_x$ | 61.18 | 47.86 | 29.28 |
| A7 | $VP_{1.2}Cu_{0.026}Ce_{0.026}Li_{0.039}O_x$ | 59.43 | 49.12 | 29.19 |
| A8 | $VP_{1.2}Cu_{0.026}Te_{0.026}Ni_{0.03}Li_{0.039}O_x$ | 63.83 | 46.36 | 29.59 |
| A9 | $VP_{1.2}Cu_{0.026}Te_{0.026}W_{0.056}Li_{0.039}O_x$ | 52.43[2] | 45.09 | 23.64 |
| A10 | $VP_{1.2}Cu_{0.026}Cr_{0.026}Te_{0.052}Li_{0.039}O_x$ | 84.75 | 52.17 | 44.22 |
| A11 | $VP_{1.185}Cu_{0.072}Te_{0.018}Na_{0.017}O_x$ | 73 | 48 | 35 |
| A12 | $VP_{1.185}Cu_{0.072}Te_{0.018}Ba_{0.017}$ | 64 | 44 | 28 |
| A13 | $VP_{1.185}Cu_{0.072}Te_{0.018}Mg_{0.937}$ | 73 | 41 | 30 |

[1] N-butane purity 99 mol %
[2] Feed contained 1 part air, 2 parts $N_2$

TABLE III

| Example | Atom Ratio P/V | Wt. % $Nb_2O_5$ Carrier | Temperature °C Salt Bath | Temperature °C Hot Spot | Product Yield Mol % $CO + CO_2$ | Product Yield Mol % MA | Product Yield Mol % Unreacted Butane |
|---|---|---|---|---|---|---|---|
| B1[1] | 1.14 | 50 | 435 | 447 | 36.5 | 48.5 | 11.5 |
| B2[2] | 1.13 | 50 | 446 | 475 | 29 | 40.5 | 27 |
| B3[3] | 1.25 | 50 | 442 | 445 | 37.4 | 48.2 | 20 |
| B4[4] | 0.90 | 40 | 447 | 457 | 52.6 | 15.2 | 32 |
| B5[5] | 1.1 | 15 | 419 | 444 | 34.7 | 48.6 | 16 |
| B6[6] | 0.90 | 50 | 437 | 445 | 53 | 3.3 | 43 |
| B7[7] | 1.11 | 10 | 438 | 460 | 31.7 | 51.2 | 13.5 |
| B8[8] | 1.0 | 40 | 420 | 425 | 38 | 6.6 | 55 |
| B9[9] | 1.16 | 2 | 437 | 448 | 41.2 | 42.7 | 16.1 |
| B10[10] | 0.90 | 50 | 430 | 445 | 54 | 1.8 | 45 |

Footnote: Table of Catalyst Complex Compositions of Table III

| Footnote | Atomic Ratios $V_2O_5$ | $P_2O_5$ | CuO | $TeO_3$ | $Li_2O$ | Wt. % and Additional Components |
|---|---|---|---|---|---|---|
| 1 | 44 | 50 | 3.0 | 1.0 | 2.0 | None |
| 2 | 43.46 | 48.94 | 2.2 | 2.2 | 3.3 | None |
| 3 | 42 | 52 | 3.5 | .5 | 2.0 | None |
| 4 | 48.5 | 43.69 | 2.2 | 2.2 | 3.3 | $Cr_2O_3$ 2 wt. % |
| 5 | 45 | 49.5 | 1.5 | 1.5 | 1.0 | $CrO_3$ 0.4 wt. % |
| 6 | 48.5 | 43.69 | 2.2 | 2.2 | 3.3 | $Co_2O_3$ 2 wt. % |
| 7 | 44.8 | 49.7 | 3.0 | 1.5 | 1.0 | $CoCl_2.6H_2O$ 1.1 wt. % |
| 8 | 46.1 | 46.1 | 2.2 | 2.2 | 3.3 | $WO_3$ 10 wt. % |
| 9 | 43.8 | 50.7 | 3.0 | 1.5 | 1.0 | $WO_3$ 13 wt. % |
| 10 | 48.5 | 43.7 | 2.2 | 2.2 | 3.3 | $MnO_2$ 2 wt. % |

TABLE IV

| Example | Wt. % Actives Based on Total Weight of Actives and Carrier[6] | Temperature °C Salt | Temperature °C Hot Spot | Atomic Ratio P/V | yield mold% $CO + CO_2$ | yield mold% MA | yield mold% Unreacted Butane |
|---|---|---|---|---|---|---|---|
| B11[1] | 50 | 446 | 475 | 1.13 | 29 | 40.5 | 27 |
| B12[2] | 50 | 435 | 447 | 1.14 | 36.5 | 48.5 | 11.5 |
| B13[3] | 80 | 411 | 432 | 1.10 | 35 | 52.8 | 13.1 |
| B14[4] | 92.5 | 427 | 436 | 1.18 | 29.4 | 55.6 | 15 |
| B15[5] | 95 | 423 | — | 1.11 | 31.9 | 53.4 | 15 |

Footnote to Table IV Catalyst Complex Composition
Atomic Ratios (No Additives)

| Footnote | $V_2O_5$ | $P_2O_5$ | CuO | $TeO_3$ | $Li_2O$ |
|---|---|---|---|---|---|
| 1 | 43.46 | 48.94 | 2.2 | 2.2 | 3.3 |
| 2 | 44 | 50 | 3.0 | 1.0 | 2.0 |
| 3 | 45 | 49.5 | 3.0 | 1.5 | 1.0 |
| 4 | 41.86 | 49.63 | 6.0 | 1.5 | 1.0 |
| 5 | 44.8 | 49.7 | 3.0 | 1.5 | 1.0 |

[6] Carrier $Nb_2O_5$

TABLE V

| Example | Wt. % Carrier[1] | Catalyst Complex Atomic Ratio | | | | | | Temperature °C | | Yield | | |
|---|---|---|---|---|---|---|---|---|---|---|---|---|
| | | $V_2O_5$ | $P_2O_5$ | CuO | $TeO_3$ | $Li_2O$ | Wt. % | Salt | Hot Spot | Mol % Co + $CO_2$ | MA | Unreacted Butane |
| B16 | 55[2] | 43 | 52 | 2.5 | 1.5 | 2.0 | — | 440 | 447 | 29 | 28 | 43 |
| B17 | 15 | 45 | 49.5 | 3.0 | 1.5 | 1.0 | $CrO_3$ 0.5% | 419 | 444 | 34.7 | 48.6 | 16 |
| B18 | 7.5 | 45.5 | 50.5 | 3.0 | 0 | 1.0 | $MnO_2$ 0.8% | 407 | 438 | 28.6 | 53.6 | 17.7 |
| B19 | 7.5 | 45.5 | 50.5 | 3.0 | 0 | 1.0 | $MoO_3$ 1.0% | 408 | 450 | 30 | 51.5 | 18 |
| B20 | 7.5 | 43.6 | 50.6 | 5.0 | 0 | .8 | $MoO_3$-0.55%$Ni_2O_3$-0.3% | 407 | 422 | 28 | 52.5 | 19 |
| B21 | 20 | 42 | 42.5 | 3.0 | 1.5 | 1.0 | $Sb_2O_3$ - 15% | 412 | 428 | 45 | 31.5 | 24 |
| B22 | 15 | 45 | 49.5 | 3.0 | 1.5 | 1.0 | $NH_4ReO_4$ - 0.67% | 430 | 443 | 35.7 | 57.4 | 6.9 |
| B23 | 2 | 43.8 | 50.7 | 3.0 | 1.5 | 1 | $WO_3$ 13% | 437 | 448 | 41.2 | 42.7 | 16.1 |
| B24 | 0 | 43 | 51 | 3.0 | 1.0 | 2.0 | $SnO_2$ 50% | 447 | 455 | 44 | 40.7 | 15.2 |
| B25 | 10 | 44.8 | 49.7 | 3.0 | 1.5 | 1.0 | $Ni_2O_3$ 0.85% | 415 | 452 | 30.9 | 51.3 | 18 |
| B26 | 7.5 | 43.1 | 50.1 | 5.0 | 1.0 | 0.8 | $Ni_2O_3$-0.3%$Re_2O_7$-0.3% $MoO_3$ - 0.06% | 403 | — | 31.2 | 53.4 | 15.4 |
| B27 | 7.5 | 43.5 | 50.5 | 5.0 | 0 | 1.0 | $PdCl_2$ - 0.09% | 425 | 445 | 33.3 | 48.7 | 18 |
| B28 | 7.5 | 44.7 | 50.3 | 5.0 | 0 | 0 | $Ag_2O$ - 0.9% | 436 | 442 | 56 | 24 | 20 |
| B29 | 7.5 | 44.7 | 50.3 | 5.0 | 0 | 0 | $CeO_2$ - 0.9% | 406 | 430 | 33 | 46.5 | 21 |
| B30 | 0 | 43.3 | 50.2 | 4.5 | 1.0 | 1.0 | $Ni_2O_3$-0.6%$Ta_2O_5$-5% | 430 | 457 | 31 | 50 | 19 |
| B31 | 7.5 | 44.7 | 50.3 | 5.0 | 0 | 0 | $HfO_2$ 2% | 399 | 438 | 25.5 | 50 | 23 |
| B32 | 7.5 | 44.7 | 50.3 | 5.0 | 0 | 0 | $UO_2$ 0.9% | 411 | 447 | 31 | 51 | 19 |
| B33 | 15 | 45 | 49.5 | 3.0 | 1.5 | 1.0 | $ZrOSO_4$ 1.4% | 424 | 445 | 39.6 | 50.1 | 10.2 |
| B34 | 7.5 | 44.7 | 50.3 | 5.0 | 0 | 0 | $ThO_2$ 2.16% | 419 | 450 | 30.0 | 47.5 | 24 |
| B35 | 7.5 | 44.7 | 50.3 | 5.0 | 0 | 0 | $HfO_2$ 2.2 BaO 1% | 408 | 423 | 34 | 47 | 18 |

[1] Unless specified otherwise the carrier is $Nb_2O_5$
[2] Carrier is $WO_3$

The invention claimed is:

1. An improved vanadium-phosphorus-oxygen catalyst complex for the oxidation of n-$C_4$ hydrocarbons to produce maleic anhydride, consisting essentially of active components in the atom ratios vanadium 1 : phosphorus 0.90 to 1.3 : copper 0.005 to 0.3 : Me 0.005 to 0.25 wherein Me consists essentially of Te said catalyst complex further containing as an active component an alkali or alkaline earth metal in the atomic ratio of 0.001 to 0.1 per atom of V.

2. An improved vanadium-phosphorous-oxygen catalyst complex for the oxidation of n-$C_4$ hydrocarbons to produce maleic anhydride, consisting essentially of active components in the atom ratios vanadium 1 : phosphorus 0.90 to 1.3 : copper 0.005 to 0.3 : Me 0.005 to 0.25 wherein Me is Te and Hf.

3. An improved vanadium-phosphorus-oxygen catalyst complex for the oxidation of n-$C_4$ hydrocarbons to produce maleic anhydride, consisting essentially of active components in the atom ratios vanadium 1 : phosphorus 0.90 to 1.3 : copper 0.005 to 0.3 : Me 0.005 to 0.25 wherein Me consists essentially of U.

* * * * *